United States Patent
Hasegawa et al.

(10) Patent No.: US 10,502,947 B2
(45) Date of Patent: Dec. 10, 2019

(54) OPTICAL FIBER SCANNING APPARATUS AND OPTICAL SCANNING TYPE ENDOSCOPE

(71) Applicant: OLYMPUS CORPORATION, Tokyo (JP)

(72) Inventors: Mamoru Hasegawa, Nagano (JP); Masanori Ogata, Nagano (JP); Hiroyoshi Yajima, Sagamihara (JP)

(73) Assignee: OLYMPUS CORPORATION, Tokyo (JP)

( * ) Notice: Subject to any disclaimer, the term of this patent is extended or adjusted under 35 U.S.C. 154(b) by 341 days.

(21) Appl. No.: 15/337,023

(22) Filed: Oct. 28, 2016

(65) Prior Publication Data

US 2017/0042410 A1 Feb. 16, 2017

Related U.S. Application Data

(63) Continuation of application No. PCT/JP2015/058287, filed on Mar. 19, 2015.

(30) Foreign Application Priority Data

May 2, 2014 (JP) .................. 2014-095334

(51) Int. Cl.
*G02B 26/10* (2006.01)
*H01F 41/04* (2006.01)
(Continued)

(52) U.S. Cl.
CPC .............. *G02B 26/103* (2013.01); *A61B 1/00* (2013.01); *A61B 1/00158* (2013.01);
(Continued)

(58) Field of Classification Search
CPC ............ A61B 1/00158; A61B 1/00165; A61B 1/00172; G02B 26/101; G02B 26/103; H01F 29/292; H01F 41/041
(Continued)

(56) References Cited

U.S. PATENT DOCUMENTS 3,702,450 A * 11/1972 Avery .................... H01F 41/041
335/213
7,129,472 B1 * 10/2006 Okawa ............... A61B 1/00059
250/234

(Continued)

FOREIGN PATENT DOCUMENTS

CN 101755233 A 6/2010
JP 2008-116922 A 5/2008
(Continued)

OTHER PUBLICATIONS

International Search Report dated May 26, 2015 issued in PCT/JP2015/058287.

*Primary Examiner* — Aaron B Fairchild
(74) *Attorney, Agent, or Firm* — Scully, Scott, Murphy & Presser P.C.

(57) ABSTRACT

An optical fiber scanning apparatus is the optical fiber scanning apparatus for which an optical fiber to which a permanent magnet is disposed and which is configured to emit illumination light from a distal end portion is arranged in a hollow portion of a magnetic field generation unit, the magnetic field generation unit is provided with four coil units each including a flexible substrate where a planar coil, a lead-out wiring layer of the planar coil and an external connection electrode pad are disposed, and an inside of the four coil units arranged in a square prism shape configures the hollow portion.

17 Claims, 13 Drawing Sheets

(51) Int. Cl.
*H01F 27/29* (2006.01)
*A61B 1/00* (2006.01)

(52) U.S. Cl.
CPC ...... *A61B 1/00165* (2013.01); *A61B 1/00172* (2013.01); *H01F 27/292* (2013.01); *H01F 41/041* (2013.01)

(58) Field of Classification Search
USPC .......................................................... 250/234
See application file for complete search history.

(56) References Cited

U.S. PATENT DOCUMENTS

| | | | | |
|---|---|---|---|---|
| 2006/0013528 | A1* | 1/2006 | Rosman | B82Y 35/00 385/25 |
| 2009/0015894 | A1* | 1/2009 | Rosman | A61B 5/0062 359/199.1 |
| 2010/0207015 | A1* | 8/2010 | Bierhoff | A61B 5/0062 250/227.26 |
| 2015/0331233 | A1* | 11/2015 | Shimamoto | G02B 26/103 385/6 |
| 2015/0338646 | A1* | 11/2015 | Innami | G02B 23/26 359/213.1 |
| 2016/0187647 | A1* | 6/2016 | Fujiwara | G02B 26/103 359/199.3 |
| 2017/0049304 | A1* | 2/2017 | Karaki | A61B 1/00158 |
| 2018/0153382 | A1* | 6/2018 | Ogata | G02B 23/26 |
| 2018/0325362 | A1* | 11/2018 | Tosaka | A61B 1/00 |
| 2018/0353056 | A1* | 12/2018 | Tosaka | G02B 26/10 |

FOREIGN PATENT DOCUMENTS

| | | |
|---|---|---|
| JP | 2010-9035 A | 1/2010 |
| JP | 2014-081484 A | 5/2014 |
| WO | WO 2014/061354 A1 | 4/2014 |
| WO | WO-2014061354 A1 * | 4/2014 ........... G02B 26/103 |

* cited by examiner

FIG. 6A
FIG. 6B
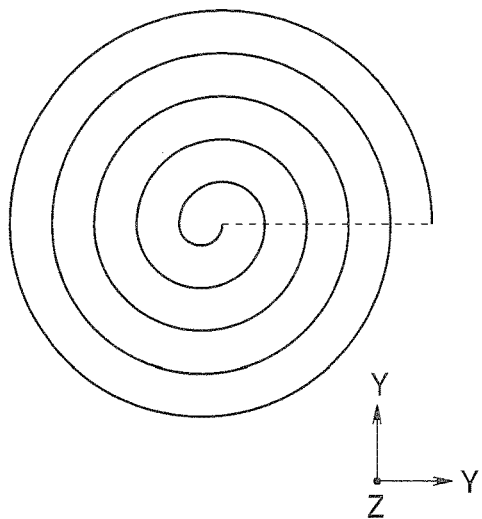
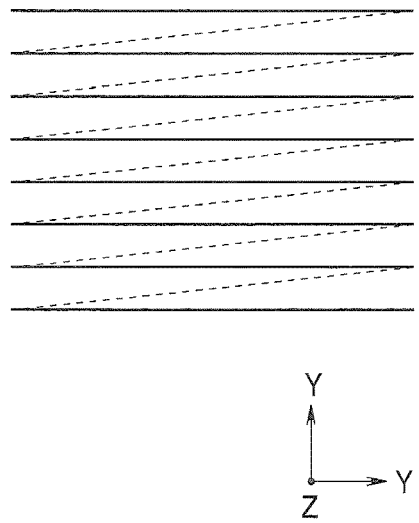
FIG. 7
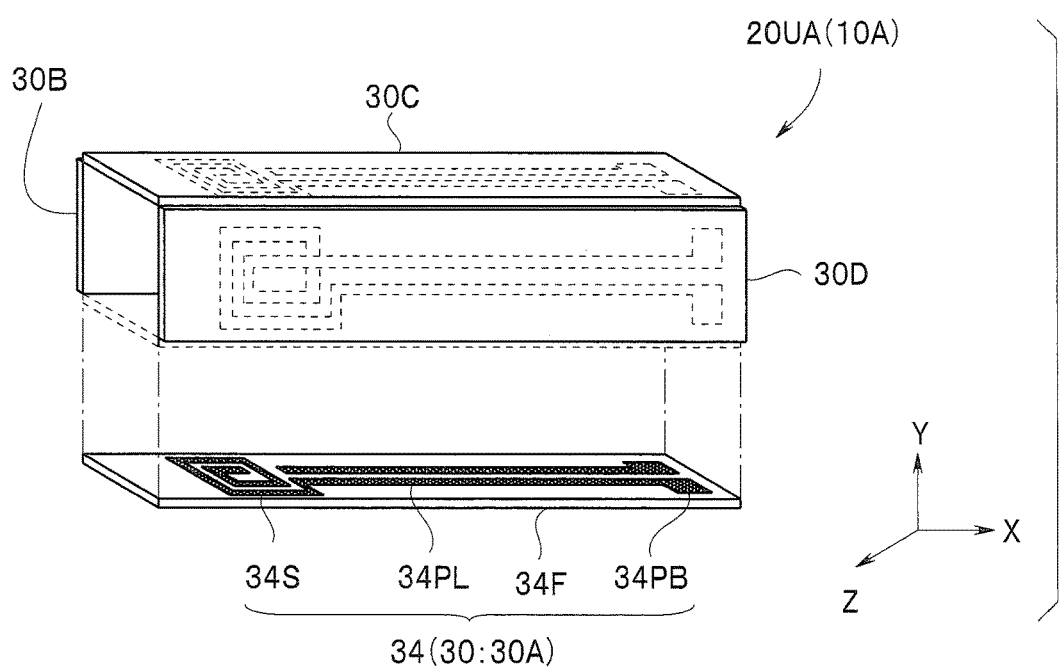

OPTICAL FIBER SCANNING APPARATUS AND OPTICAL SCANNING TYPE ENDOSCOPE

CROSS REFERENCE TO RELATED APPLICATION

This application is a continuation application of PCT/JP2015/058287 filed on Mar. 19, 2015 and claims benefit of Japanese Application No. 2014-095334 filed in Japan on May 2, 2014, the entire contents of which are incorporated herein by this reference.

BACKGROUND OF THE INVENTION

1. Field of the Invention

The present invention relates to an optical fiber scanning apparatus including a frame body to which a magnetic field generation unit is disposed, and an optical fiber in which a permanent magnet is disposed and which emits light from a distal end portion, and an optical scanning type endoscope including the optical fiber scanning apparatus at a distal end portion of an insertion portion.

2. Description of the Related Art

An image pickup apparatus using an image pickup device such as a CCD or a CMOS image sensor simultaneously receives reflected light from a subject by many photodetectors arranged in a matrix shape, and acquires an object image. In the case of an endoscope which photographs a dark inside of a body, an image in a range illuminated by light from a light source is acquired.

In contrast, in an optical scanning type image pickup apparatus, while an object is scan-irradiated by a light spot, the reflected light is successively received, and an object image is prepared based on the light reception data.

For example, in the optical scanning type image pickup apparatus, by an optical fiber scanning apparatus two-dimensionally scanning a distal end portion of an optical fiber that guides light from a light source, scan irradiation of the light spot is performed.

Optical fiber scanning of the optical fiber scanning apparatus is performed by controlling magnetic application from a magnetic field generation unit to an optical fiber where a magnet is disposed, for example.

Further, in an endoscope, diameter reduction of a distal end portion is strongly demanded in order to reduce invasion. In order to reduce a diameter of an optical scanning type endoscope for which an optical fiber scanning apparatus is disposed at a distal end portion, the diameter reduction of the optical fiber scanning type image pickup apparatus is an important issue.

Japanese Patent Application Laid-Open Publication No. 2008-116922 discloses an optical fiber scanning apparatus using magnetic force. In the conventional optical fiber scanning apparatus, an optical fiber where a permanent magnet is disposed is arranged at a center of a magnetic field generation unit formed of four electromagnets (magnetic field generation portions) which are orthogonally arranged/oppositely arranged inside a cylinder.

In the optical fiber scanning apparatus, a coil of the electromagnet is a winding coil in which a copper wire is wound in an elliptic shape around an outer periphery of a magnetic core formed of a soft magnetic body.

SUMMARY OF THE INVENTION

An optical fiber scanning apparatus of an embodiment includes: a frame body with a hollow portion, a cross section in a long axis direction of which is square and a distal end of which is an opening; and a magnetic field generation unit, and an optical fiber to which a permanent magnet is disposed and which is configured to emit illumination light from a distal end portion, which are disposed in the hollow portion of the frame body, the magnetic field generation unit is provided with four coil units each including a flexible substrate where two planar coils lined in the long axis direction, a lead-out wiring layer of the two planar coils and an external connection electrode pad extended from a rear end of the lead-out wiring layer are disposed, the four coil units are disposed on inner surfaces of the hollow portion, and an incidence portion of a detection unit configured to detect reflected light of the illumination light emitted from the optical fiber is arranged at a distal end portion of the frame body.

In addition, an optical fiber scanning apparatus of another embodiment is the optical fiber scanning apparatus for which an optical fiber to which a permanent magnet is disposed and which is configured to emit illumination light from a distal end portion is arranged in a hollow portion of a magnetic field generation unit, the magnetic field generation unit is provided with four coil units each including a flexible substrate where a planar coil, a lead-out wiring layer of the planar coil and an external connection electrode pad extended from a rear end of the lead-out wiring layer are disposed, and an inside of the four coil units arranged in a square prism shape configures the hollow portion.

Further, an optical scanning type endoscope of another embodiment has, at a distal end portion of an insertion portion, the optical fiber scanning apparatus for which an optical fiber to which a permanent magnet is disposed and which is configured to emit illumination light from a distal end portion is arranged in a hollow portion of a magnetic field generation unit, wherein the magnetic field generation unit is provided with four coil units each including a flexible substrate where a planar coil, a lead-out wiring layer of the planar coil and an external connection electrode pad extended from a rear end of the lead-out wiring layer are disposed, and an inside of the four coil units arranged in a square prism shape configures the hollow portion.

BRIEF DESCRIPTION OF THE DRAWINGS

FIG. 6A is a diagram for explaining a scanning method of the optical fiber scanning apparatus in the first embodiment;

FIG. 6B is a diagram for explaining the scanning method of the optical fiber scanning apparatus in the first embodiment;

FIG. 7 is a perspective view of a magnetic field generation unit of the optical fiber scanning apparatus in a modification 1 of the first embodiment;

DETAILED DESCRIPTION OF THE PREFERRED EMBODIMENTS

First Embodiment

Figure 1:
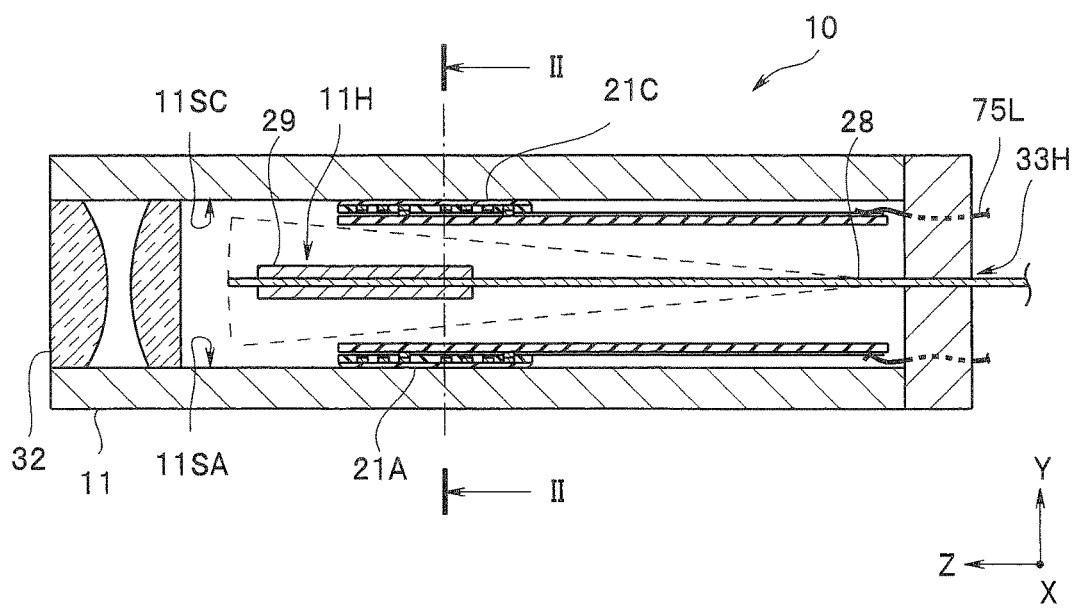
FIG. 1 is a sectional view along a center line of an optical fiber scanning apparatus in a first embodiment.
Figure 2:
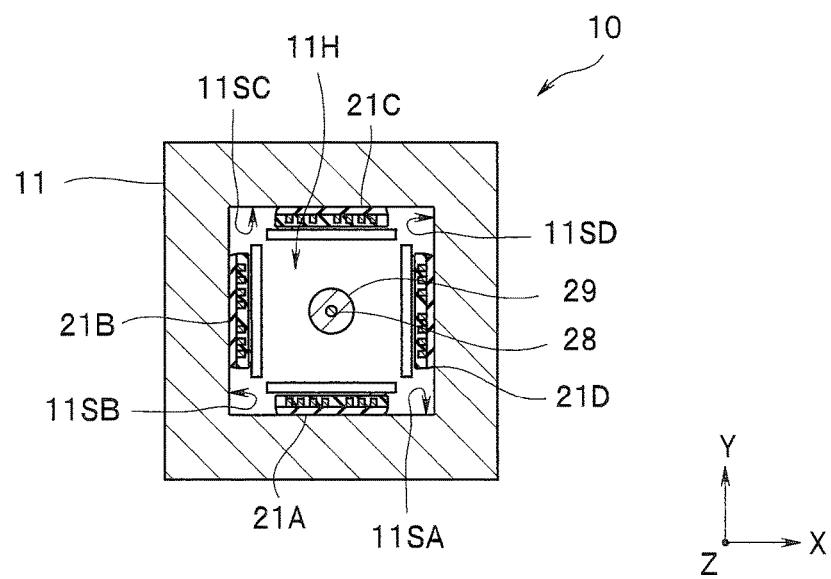
FIG. 2 is a sectional view along a II-II line in FIG. 1 of the optical fiber scanning apparatus in the first embodiment.

Using FIG. 1 to FIG. 3, an optical fiber scanning apparatus 10 in the first embodiment will be described. Note that, in a following description, drawings based on respective embodiments are schematic, it is to be taken into consideration that relations between thicknesses and widths of respective portions and ratios of the thicknesses of the respective portions or the like are different from actual ones, and portions where mutual dimensional relations or ratios are different are sometimes included among the drawings.

The optical fiber scanning apparatus 10 has a frame body 11, an optical fiber 28 arranged along a center line O in a long axis (Z axis) direction of a hollow portion 11H of the frame body 11, a magnetic field generation unit 20U provided with four coil units 20A to 20D, and an illumination optical system 32.

The optical fiber 28 guides light from a light source unit 174 (see FIG. 21) and emits illumination light from a distal end portion. The illumination light spot-irradiates an object through the illumination optical system 32 formed of a plurality of lenses. Note that the illumination optical system 32 is not an essential component.

To a rear portion of the distal end portion of the optical fiber 28, a permanent magnet 29 is bonded by an adhesive or the like. For example, the permanent magnet 29 formed of an SmCo alloy is a cylindrical type and is magnetized in a longitudinal direction. The optical fiber 28 is inserted through a through-hole 33H of a holding member 33, and is bonded to the holding member 33. The distal end portion of the optical fiber 28 to which a bond portion (proximal end portion) of the holding member 33 is fixed is movable within an XY plane vertically and horizontally with the proximal end portion as a base point.

The frame body 11 has the hollow portion 11H, a cross section of which orthogonal to the center line O is square. It is preferable that the frame body 11 is formed of a metal for accurate processing, and it is especially preferable that the frame body 11 is formed of stainless steel or an aluminum alloy which is excellent in machinability and weather resistance. In addition, from a viewpoint of magnetic flux leakage reduction or the like, it is also especially preferable that the frame body 11 is formed of a soft magnetic material of high magnetic permeability such as permalloy.

A coil unit 20A is bonded by an adhesive or the like for example to a first surface 11SA of the hollow portion 11H of the frame body 11, and a coil unit 20B is bonded to a second surface 11SB. Similarly, a coil unit 20C is bonded to a third surface 11SC, and a coil unit 20D is bonded to a fourth surface 11SD. The coil units 20A to 20D are in a same configuration. Note that, hereinafter, each of the coil units 20A to 20D is referred to as a coil unit 20.

Figure 3:
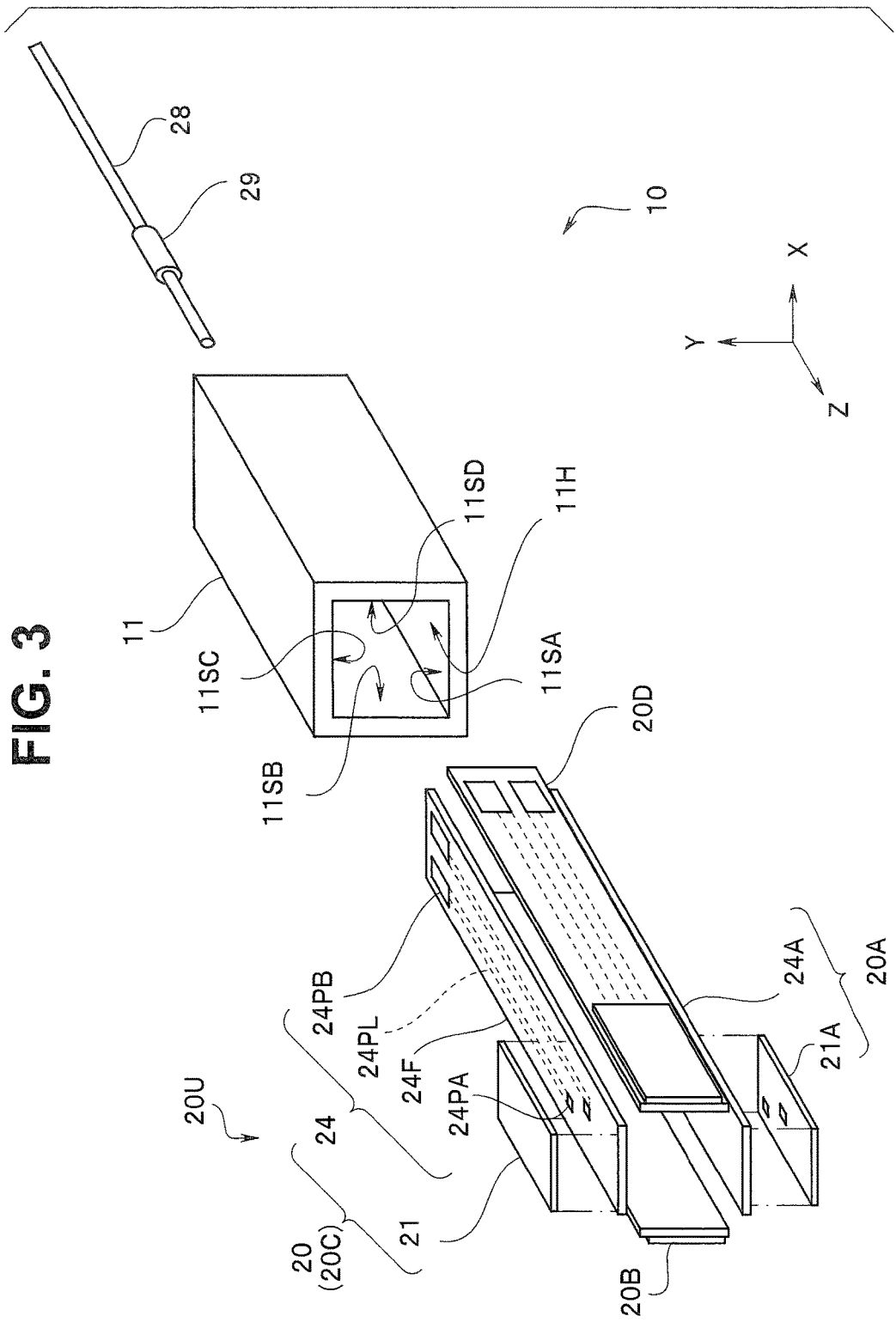
FIG. 3 is an exploded view of a main section of the optical fiber scanning apparatus in the first embodiment.
Figure 4:
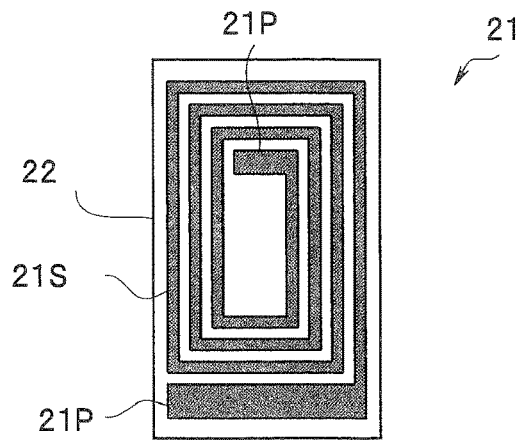
FIG. 4 is a top view of a planar coil of the optical fiber scanning apparatus in the first embodiment.

As illustrated in FIG. 3 and FIG. 4 or the like, the coil unit 20 is formed of a wiring board 24 on which a coil chip 21 including a planar coil 21S is flip-chip-mounted.

For the coil chip 21, to a base body 22 formed of silicon, the planar coil 21S which is a drive coil in a spiral shape is disposed through an insulating layer of a silicon oxide or the like (not shown in the figure). The planar coil 21S is covered with an insulating layer 23 formed of a resin such as polyimide or epoxy except for contact hole portions at an upper part of a bond pad 21P at both ends. The illustrated planar coil 21S includes a conductor layer (planar coil) formed of a patterned low resistance metal such as copper or gold and an insulating layer covering the conductor layer.

Note that, while a bond pad is arranged also at a coil center in the coil chip 21, in order to provide the bond pad around the coil, one insulating layer/lead-out wiring layer may be provided further, or the coil chip 21 may be a multilayer coil in which a plurality of coils are laminated through the insulating layer.

The coil chip 21 can be manufactured by disposing many planar coils on a silicon wafer and then dividing the planar coils by a MEMS semiconductor process. By using a highly accurate resist mask manufactured by a photolithographic method using photoresist and a photomask and performing patterning by an additive method, a subtraction method or the like, the coil chip 21 including the planar coil 21S with high accuracy can be easily manufactured in large quantities.

The wiring board 24 is a flexible wiring board in which a coil connection electrode pad 24PA, an external connection electrode pad 24PB, and a lead-out wiring layer 24PL which connects the coil connection electrode pad 24PA and the external connection electrode pad 24PB are disposed to a flexible substrate 24F.

In order to dispose the lead-out wiring layer 24PL or the like to the flexible substrate 24F formed of an insulating resin such as polyimide, a conventional printed wiring board manufacturing method is used. For example, the wiring board 24 is manufactured by forming an etching mask on a polyimide substrate to which copper foil is bonded and then etching the copper foil. That is, the coil connection electrode pad 24PA, the external connection electrode pad 24PB and the lead-out wiring layer 24PL are formed of an integrated copper layer.

To the coil connection electrode pad 24PA and the external connection electrode pad 24PB, a connection pad formed of nickel/gold or the like may be disposed on the copper layer. In addition, an area excluding the coil connection electrode pad 24PA and the external connection electrode pad 24PB of the wiring board 24 may be covered with the insulating layer. In addition, in a case that the wiring board 24 is a multilayer wiring board, the coil connection electrode pad 24PA and the external connection electrode pad 24PB may be disposed on different main surfaces.

To the coil connection electrode pad 24PA of the wiring board 24, the bond pad 21P of the coil chip 21 is bonded. To the external connection electrode pad 24PB of the wiring board 24, wiring 75L connected with a drive control unit 175 (see FIG. 21) which supplies a driving current is bonded. The planar coil 21S generates a magnetic field in a direction orthogonal to the main surface of the coil chip 21 when the driving current is applied to the bond pad 21P. Strength of the magnetic field is set by a current value of the driving current and a number of turns of a spiral coil or the like. When a direction of the driving current flowing through the coil is inverted, the direction of the generated magnetic field is inverted.

As already described, in the hollow portion 11H of the frame body 11, the magnetic field generation unit 20U provided with the four coil units 20 each including the planar coil 21S is disposed. That is, planar coils 21S1 and 21S2 are disposed respectively on the first surface 11SA and the second surface 11SB of the frame body 11, and planar coils 21S3 and 21S4 are disposed respectively on the third surface 11SC and the fourth surface 11SD which are orthogonal to each other. That is, the planar coil 21S1 and the planar coil 21S3 are arranged at opposite positions, and the planar coil 21S2 and the planar coil 21S4 are arranged at opposite positions.

Therefore, the planar coils 21S1 and 21S3 generate the magnetic field in an X axis direction, and the planar coils 21S2 and 21S4 generate the magnetic field in a Y axis direction.

Note that, in the optical fiber scanning apparatus 10, a surface where the coil chip 21 is disposed is bonded with the frame body 11; however, an opposite surface may be bonded with the frame body 11.

Next, a driving method of the optical fiber scanning apparatus 10 will be simply described.

Figure 5A:
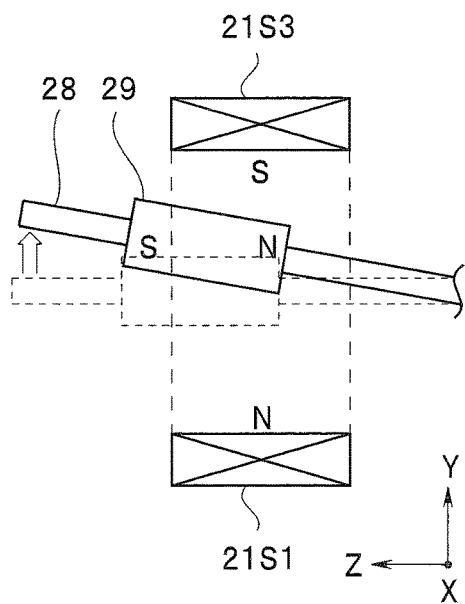
FIG. 5A is a sectional schematic diagram for explaining a driving method of the optical fiber scanning apparatus in the first embodiment.

As illustrated in FIG. 5A, when the driving current is supplied to the planar coil 21S1, for example, the magnetic field in which an inner surface side is an N pole is generated. Simultaneously, when the driving current is supplied to the planar coil 21S3, for example, the magnetic field in which the inner surface side is an S pole is generated. Then, a rear end side (N pole) of the permanent magnet 29 arranged within the magnetic field is pulled up in a Y axis upper direction. Therefore, a distal end of the optical fiber 28 is also moved in the Y axis upper direction.

Figure 5B:
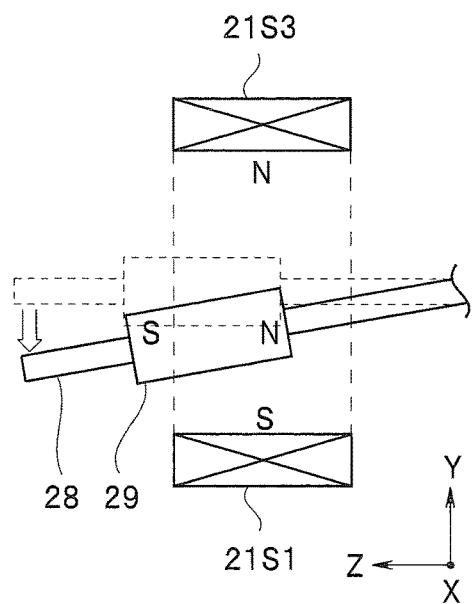
FIG. 5B is a sectional schematic diagram for explaining the driving method of the optical fiber scanning apparatus in the first embodiment.

On the other hand, as illustrated in FIG. 5B, when the driving current in the direction opposite to that in the case of FIG. 5A is supplied to the planar coil 21S1, the magnetic field in which the inner surface side is the S pole is generated. Similarly, when the driving current in the direction opposite to that in the case of FIG. 5A is supplied to the planar coil 21S3, the magnetic field in which the inner surface side is the N pole is generated. Then, the rear end side (N pole) of the permanent magnet 29 arranged within the magnetic field is pulled down in a Y axis lower direction. Therefore, the distal end portion of the optical fiber 28 is also moved in the Y axis lower direction.

Therefore, by controlling the direction of the driving current supplied to the planar coils 21S1 and 21S3, the distal end portion of the optical fiber 28 is scanned in the Y axis direction. Similarly, by controlling the direction of the driving current supplied to the planar coils 21S2 and 21S4, the distal end portion of the optical fiber 28 is scanned in the X axis direction.

Note that the permanent magnet 29, the optical fiber or the magnetic field generation unit 20U may be arranged such that the magnetic field is applied to a distal end side of the permanent magnet 29. In addition, for example, scanning is possible even when only the planar coil 21S1 and the planar coil 21S2 are driven.

By controlling the direction of the driving current supplied to the four planar coils 21S1 to 21S4, the distal end portion of the optical fiber 28 is two-dimensionally scanned within the XY plane. A scanning width is controlled by a driving current value. As a result, a light spot emitted from the distal end portion of the optical fiber 28 is two-dimensionally scanned.

As a two-dimensional scanning system, a spiral scanning system illustrated in FIG. 6A or a raster scanning system illustrated in FIG. 6B is preferable since image processing is easy, and the raster scanning system is especially preferable since illumination can be uniformly performed.

Then, the optical fiber scanning apparatus 10 has a small diameter since the magnetic field generation unit 20U is formed of extremely thin coil chips 21A to 21D, a thickness of which is equal to or larger than 10 μm and is equal to or smaller than 200 μm for example, because the planar coil is provided. Further, since the coil units 20A to 20D are respectively disposed on inner surfaces of the hollow portion 11H of the square cross section of the frame body 11, the coil units 20A to 20D are accurately oppositely arranged/orthogonally arranged.

Therefore, the optical fiber scanning apparatus 10 has the small diameter and is capable of performing highly accurate scan irradiation. Further, since the planar coil 21S (coil chip 21) of each coil unit 20 is flip-chip-mounted on the wiring board 24 including the external connection electrode pad 24PB, it is easy to connect wiring which transmits driving power.

Note that, without using the frame body 11, after arranging the coil units 20A to 20D in a square prism shape, the coil units 20A to 20D may be fixed by molding an outer peripheral portion by a resin or the like. That is, the frame body 11 is not an essential component of the optical fiber scanning apparatus 10.

Modifications of First Embodiment

Next, optical fiber scanning apparatuses 10A and 10B in modifications of the first embodiment will be described.

Since the optical fiber scanning apparatuses 10A and 10B are similar to the optical fiber scanning apparatus 10, descriptions of components of same functions are omitted. Note that, in the following diagrams, the optical fiber and the magnetic field generation unit or the like are sometimes not illustrated.

The optical fiber scanning apparatuses 10A and 10B have effects of the optical fiber scanning apparatus 10 and have further characteristic effects.

Modification 1 of First Embodiment

As illustrated in FIG. 7, in the optical fiber scanning apparatus 10A, four coil units 30 (30A to 30D) of a magnetic field generation unit 20UA is a wiring board 34 in which a planar coil 34S in the spiral shape, a lead-out wiring layer 34PL and an electrode pad 34PB are disposed to a flexible substrate 34F by a copper layer which is an integrated same material. That is, the wiring board 34 includes the planar coil 34S. The coil units 30A to 30D are in the same configuration.

The wiring board 34 where the planar coil 34S is disposed can be manufactured by the almost same method as the wiring board 24, that is, by a general purpose printed wiring board manufacturing method. Therefore, the planar coil 34S with relatively high dimension accuracy can be manufactured simultaneously with the lead-out wiring layer 34PL and the electrode pad 34PB.

For the magnetic field generation unit 20UA, the coil units 30A to 30D are arranged in the square prism shape. Note that, while a surface where the planar coil 34S or the like is disposed is an inner surface of a square prism in FIG. 7, the surface where the planar coil 34S or the like is disposed may be an outer surface of the square prism. In addition, in the case that the wiring board 34 is a double-sided wiring board, the surface where the planar coil 34S is disposed and the surface where the electrode pad 34PB is disposed may be different for example.

Note that, like the optical fiber scanning apparatus 10, the coil units 30A to 30D may be bonded to the inner surfaces of the hollow portion of the square cross section of the frame body.

Since the wiring board 34 includes the planar coil 34S, the optical fiber scanning apparatus 10A is easier to manufacture and more inexpensive than the optical fiber scanning apparatus 10.

Modification 2 of First Embodiment

Figure 8:
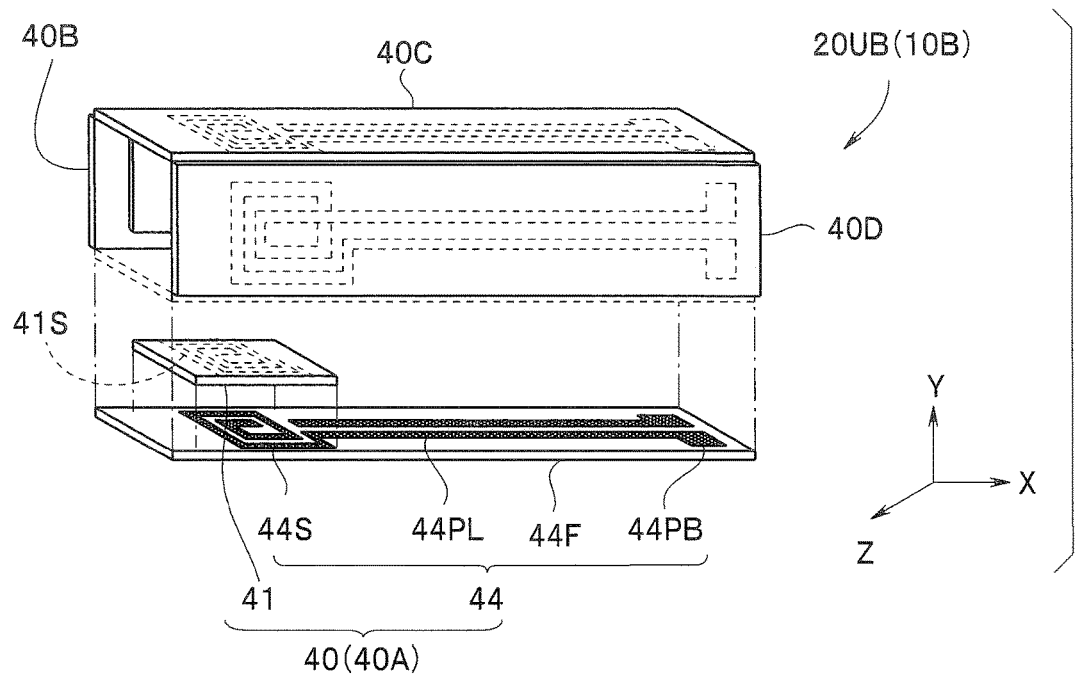
FIG. 8 is a perspective view of the magnetic field generation unit of the optical fiber scanning apparatus in a modification 2 of the first embodiment.

As illustrated in FIG. 8, in the optical fiber scanning apparatus 10B, four coil units 40 (40A to 40D) of a magnetic field generation unit 20UB includes a wiring board 44 in which a planar coil 44S is disposed to a flexible substrate 44F as a conductor layer integrated with a lead-out wiring layer 44PL and an electrode pad 44PB. That is, similarly to the optical fiber scanning apparatus 10A, the wiring board 44 includes the planar coil 44S.

Then, in the optical fiber scanning apparatus 10B, further, a coil chip 41 provided with a second planar coil 41S is flip-chip-mounted right above the planar coil 44S of the wiring board 44. That is, by disposing and connecting the second planar coil 41S of the coil chip 41, such that a center of the spiral coil coincides, on the planar coil 44S of the wiring board 44, the multilayer coil formed of the two planar coils is configured. The coil units 40A to 40D are in the same configuration.

The coil chip 41 is in the almost same configuration as the already-described coil chip 21 with the silicon as the base body.

Figure 9:
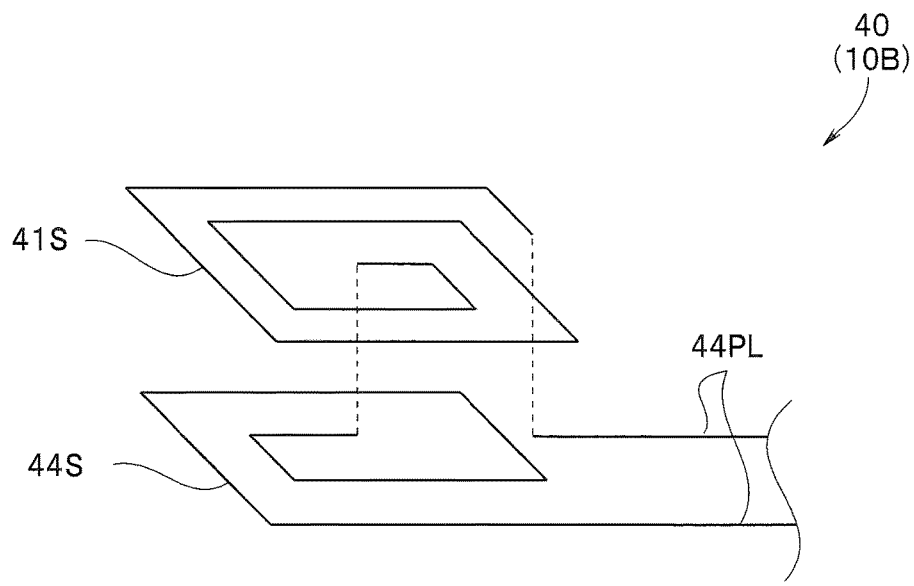
FIG. 9 is a connection diagram of two planar coils of the optical fiber scanning apparatus in the modification 2 of the first embodiment.

As illustrated in FIG. 9, the planar coil 44S of the wiring board 44 and the second planar coil 41S of the coil chip 41 are wound in the same direction, and configure the multilayer coil which generates the magnetic fields in the same direction when a current is applied.

The strength of the magnetic field generated by the spiral coil increases proportionally to the number of turns of the coil. Therefore, in order to efficiently drive the planar coil arranged within a predetermined occupancy area with low power, the multilayer coil is preferable. However, multilayer coil manufacture needs not only disposition of an insulating layer between the coils but also complicated processes such as flattening of the insulating layer with recesses and projections by the coil of a lower layer in order to guarantee dimension accuracy of the coil of an upper layer.

In the optical fiber scanning apparatus 10B, the multiplayer coil can be configured just by flip-chip-mounting the coil chip 41 to the wiring board 44. The optical fiber scanning apparatus 10B provided with the multilayer coil can be driven with lower power and with better efficiency than the optical fiber scanning apparatus 10.

Second Embodiment

Next, an optical fiber scanning apparatus 10C in a second embodiment will be described. Since the optical fiber scanning apparatus 10C is similar to the optical fiber scanning apparatus 10 or the like, the descriptions of the components of the same functions are omitted.

In the optical fiber scanning apparatus 10C, four coil units 50 (50A to 50D) of a magnetic field generation unit 20UC include two planar coils 51S1 and 51S2 lined in the long axis direction. The coil units 50A to 50D are in the same configuration.

Figure 10:
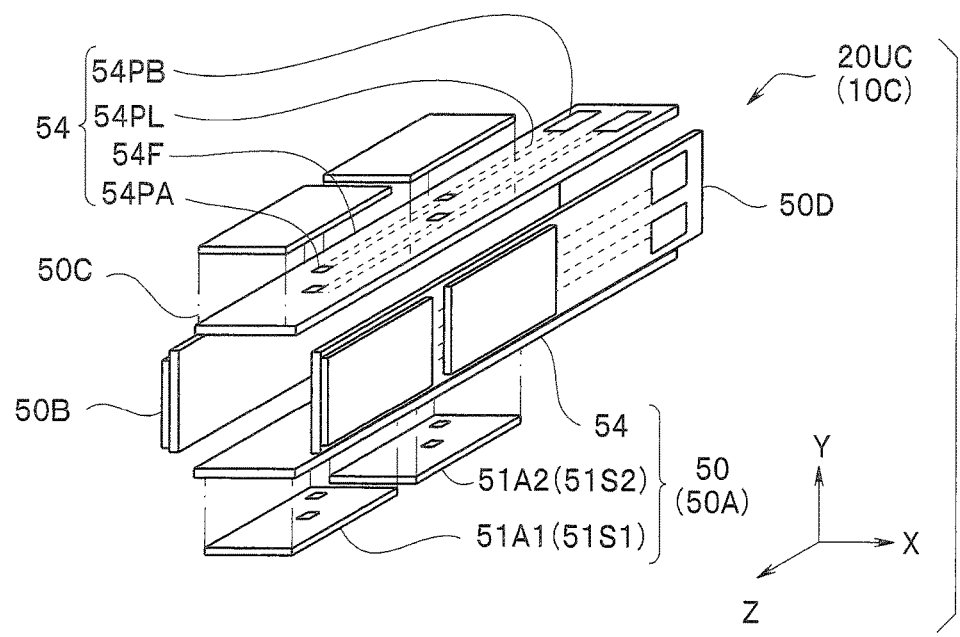
FIG. 10 is a perspective view of the magnetic field generation unit of the optical fiber scanning apparatus in a second embodiment.
Figure 11:
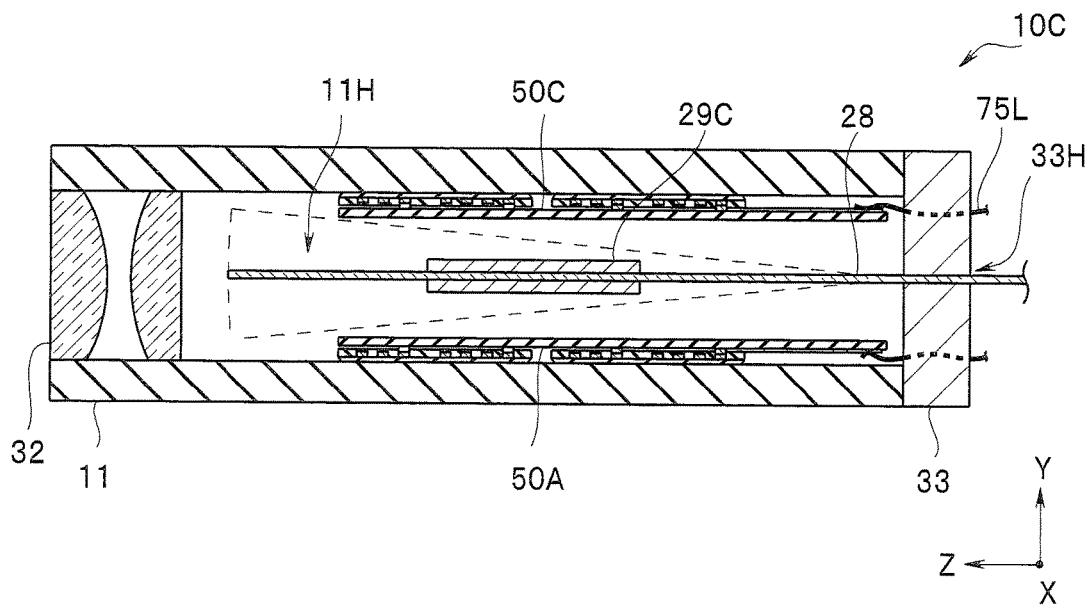
FIG. 11 is a sectional view of the optical fiber scanning apparatus in the second embodiment.

That is, as illustrated in FIG. 10 and FIG. 11, on a wiring board 54 of the coil unit 50, a coil chip 51A1 provided with a planar coil 51S1 and a coil chip 51A2 provided with a planar coil 51S2 are flip-chip-mounted. The coil chips 51A1 and 51A2 are in the almost same configuration as the coil chip 21.

A permanent magnet 29C disposed to the optical fiber 28 has an almost same length as a distance between the centers of spirals of the two planar coils 51S1 and 51S2. Note that, instead of the long permanent magnet 29C, two permanent magnets may be disposed to the optical fiber 28.

Figure 12A:
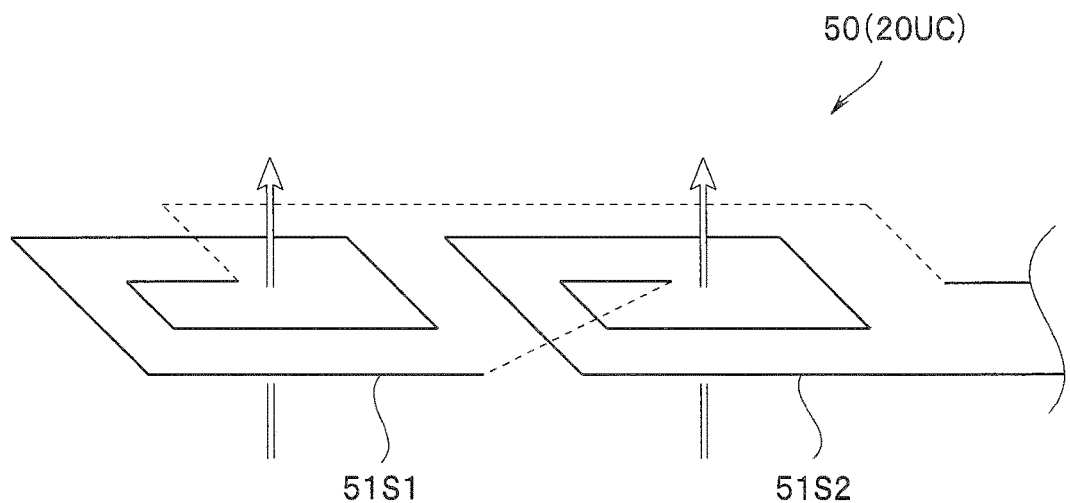
FIG. 12A is a connection diagram of two planar coils of the optical fiber scanning apparatus in the second embodiment.
Figure 12B:
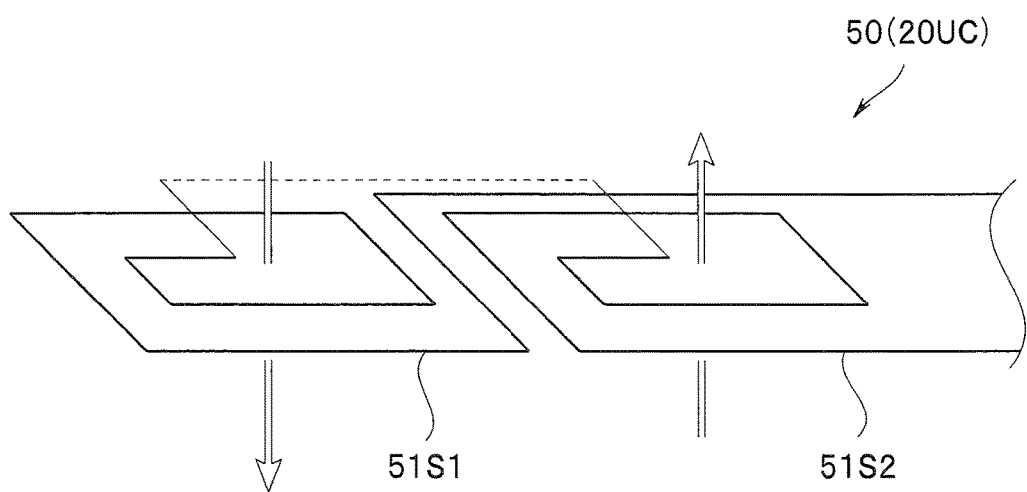
FIG. 12B is a connection diagram of two planar coils of the optical fiber scanning apparatus in the second embodiment.

As illustrated in FIG. 12A and FIG. 12B, the two serially connected planar coils 51S1 and 51S2 generate the magnetic fields in the same direction (FIG. 12A) or generate the magnetic fields in the opposite directions (FIG. 12B) depending on a difference of a connection state.

Next, a driving method of the optical fiber scanning apparatus 10C will be simply described. In the optical fiber scanning apparatus 10C, a first driving method or a second driving method can be used.

Figure 13A:
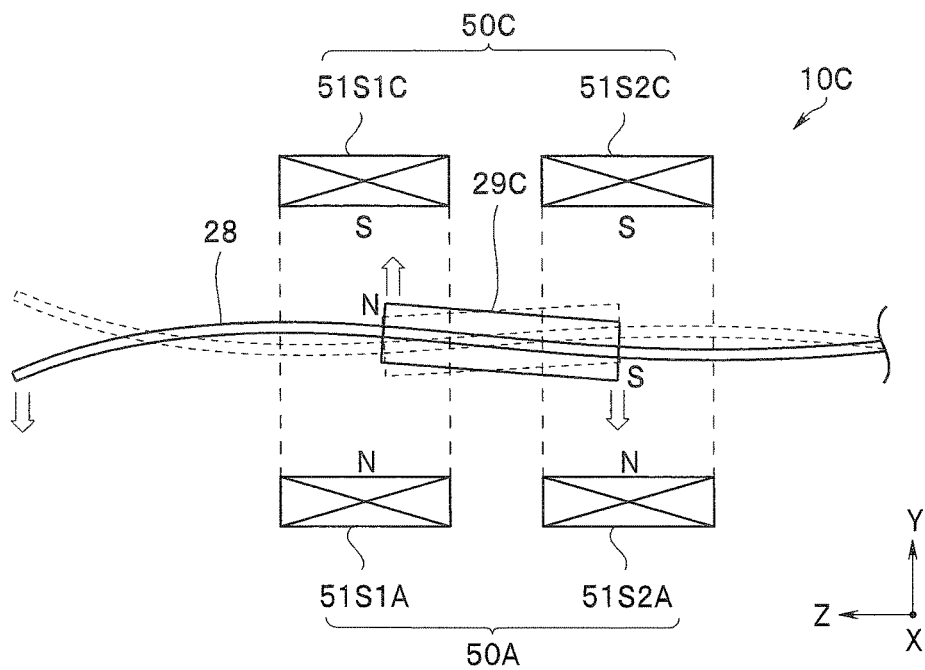
FIG. 13A is a sectional schematic diagram for explaining a driving method of the optical fiber scanning apparatus in the second embodiment.

As illustrated in FIG. 13A, in the first driving method, the two planar coils 51S1 and 51S2 of the coil unit 50 generate the magnetic fields in the same direction.

Planar coils 51S1A and 51S2A of the coil unit 50A both generate the magnetic fields in which the inner surface side is the N pole for example, and planar coils 51S1C and 51S2C of the coil unit 50C both generate the magnetic fields in which the inner surface side is the S pole for example.

The distal end side (N pole) of the permanent magnet 29C is pulled up in an upper direction (+Y direction) by the planar coils 51S1A and 51S1C. On the other hand, the rear end side (S pole) of the permanent magnet 29C receives force in a lower direction (−Y direction) by the planar coils 51S2A and 51S2C. By vibrations of the permanent magnet 29C by magnetic force from the planar coils 51S, the optical fiber 28 performs resonant vibrations of a higher mode with an antinode and a node in the longitudinal direction, a high resonance frequency is obtained by the resonant vibrations of the higher mode, and scanning at a high speed becomes possible.

Figure 13B:
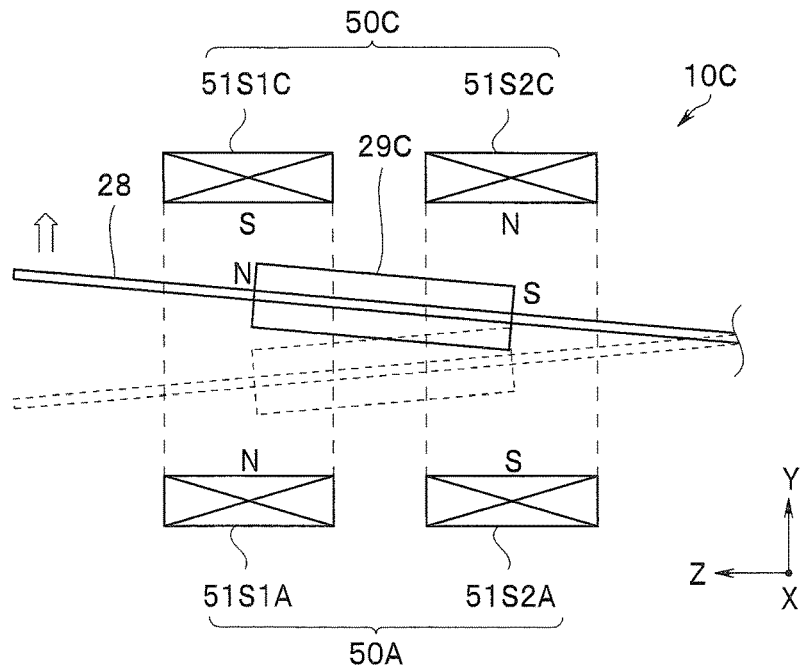
FIG. 13B is a sectional schematic diagram for explaining the driving method of the optical fiber scanning apparatus in the second embodiment.

On the other hand, as illustrated in FIG. 13B, in the second driving method, the two planar coils 51S1A and 51S2A of the coil unit 50A generate the magnetic fields in the opposite directions. In addition, the two planar coils 51S1C and 51S2C of the coil unit 50C also generate the magnetic fields in the opposite directions.

The distal end side (N pole) of the permanent magnet 29C is pulled up in the upper direction (+Y direction) by the planar coils 51S1A and 51S1C. The rear end side (S pole) of the permanent magnet 29C is also pulled up in the upper direction (+Y direction) by the planar coils 51S2A and 51S2C. Thus, the optical fiber 28 is capable of scanning of a predetermined amplitude even when the magnetic field generated by each coil is weak.

Note that, in the case that two short permanent magnets are disposed, the driving method different from the above is also possible.

Since the optical fiber scanning apparatus 10C can scan the optical fiber 28 more efficiently than the optical fiber scanning apparatus 10, power consumption is low.

Modifications of Second Embodiment

Next, optical fiber scanning apparatuses 10D to 10F in modifications of the second embodiment will be described. Since the optical fiber scanning apparatuses 10D to 10F are similar to the optical fiber scanning apparatus 10C, the descriptions of the components of the same functions are omitted.

In the optical fiber scanning apparatuses 10D to 10F, similarly to the optical fiber scanning apparatus 10C, each coil unit is provided with two planar coils lined in the long axis direction. Therefore, the optical fiber scanning apparatuses 10D to 10F have effects of the optical fiber scanning apparatus 10C and have further characteristic effects.

Modification 1 of Second Embodiment

Figure 14:
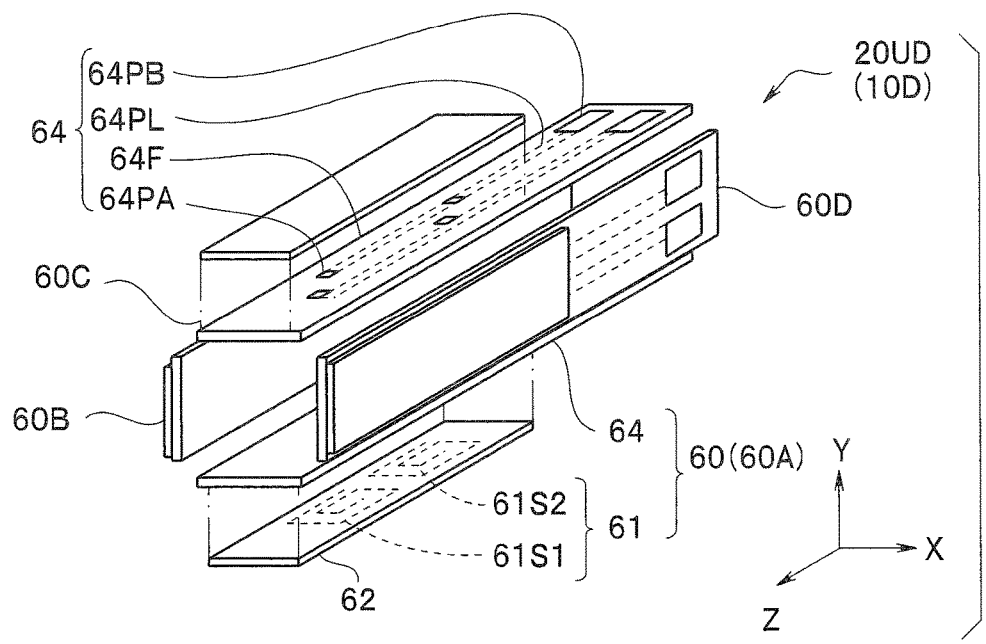
FIG. 14 is a perspective view of a magnetic field generation unit of the optical fiber scanning apparatus in a modification 1 of the second embodiment.

As illustrated in FIG. 14, in the optical fiber scanning apparatus 10D, for coil units 60 (60A to 60D) of a magnetic field generation unit 20UD, a coil chip 61 provided with a base body 62 and two planar coils 61S1 and 61S2 lined in the long axis direction of the base body 62 respectively is flip-chip-mounted on a wiring board 64. For the wiring board 64, a coil connection electrode pad 64PA, a lead-out wiring layer 64PL and an external connection electrode pad 64PB are disposed to a flexible substrate 64F as an integrated conductor layer.

Since one coil chip 61 is flip-chip-mounted on the coil unit 60, the optical fiber scanning apparatus 10D is easy to manufacture.

Modification 2 of Second Embodiment

Figure 15:
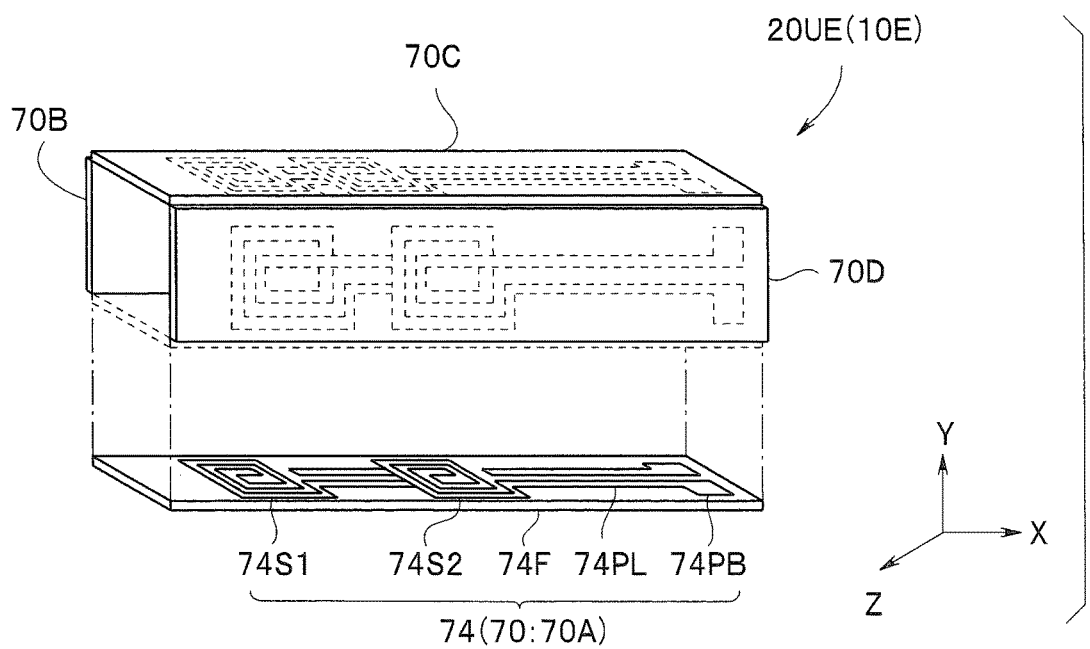
FIG. 15 is a perspective view of the magnetic field generation unit of the optical fiber scanning apparatus in a modification 2 of the second embodiment.

As illustrated in FIG. 15, in the optical fiber scanning apparatus 10E in the modification 2 of the second embodiment, coil units 70 (70A to 70D) of a magnetic field generation unit 20UE are a wiring board 74 where two planar coils 74S1 and 74S2 are lined in the long axis direction.

That is, for the wiring board 74, the two planar coils 74S1 and 74S2, a lead-out wiring layer 74PL and an external connection electrode pad 74PB are disposed to a flexible substrate 74F as an integrated conductor layer.

Since the wiring board 74 includes the two planar coils 74S1 and 74S2, manufacture is easier and it is more inexpensive than the optical fiber scanning apparatuses 10C and 10D.

Modification 3 of Second Embodiment

Figure 16:
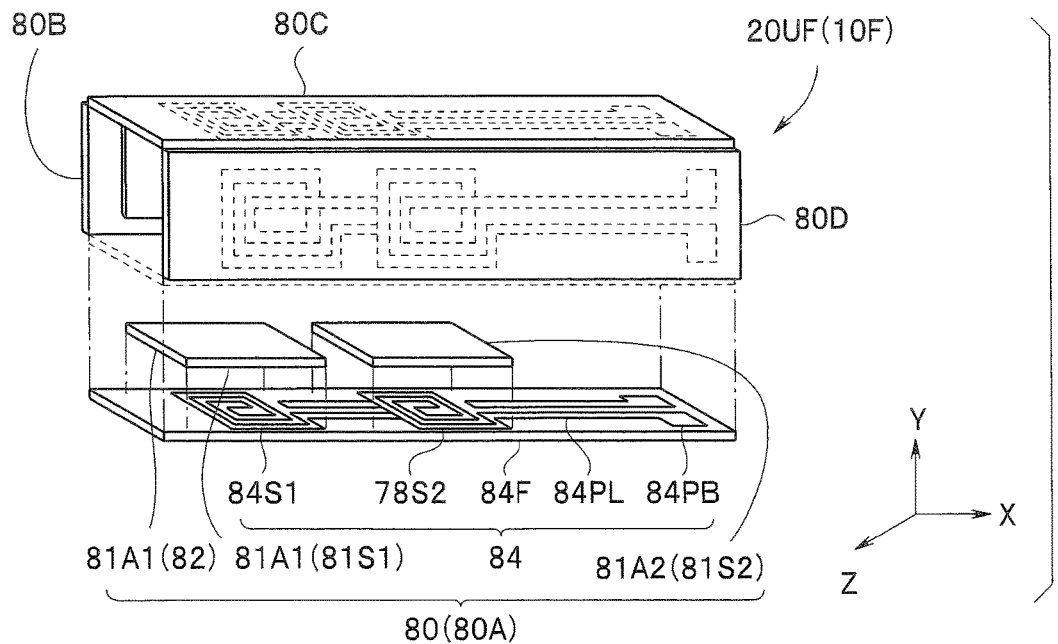
FIG. 16 is a perspective view of the magnetic field generation unit of the optical fiber scanning apparatus in a modification 3 of the second embodiment.

As illustrated in FIG. 16, in the optical fiber scanning apparatus 10F in the modification 3 of the second embodiment, for coil units 80 (80A to 80D) of a magnetic field generation unit 20UF, coil chips 81A1 and 81A2 are flip-chip-mounted further on a wiring board 84 including two planar coils 81S1 and 81S2.

A second planar coil 81S1 is disposed to the coil chip 81A1, and a second planar coil 81S2 is disposed to the coil chip 81A2. The coil units 70A to 70D are in the same configuration.

In the optical fiber scanning apparatus 10F, the coil chips 81A1 and 81A2 provided with a base body 82 and the second planar coils 81S1 and 81S2 disposed to the base body 82 are flip-chip-mounted right above each of two planar coils 84S1 and 84S2 of the wiring board 84, and each of the planar coils 84S1 and 84S2 and each of the second planar coils 81S1 and 81S2 are connected and configure the multilayer coil.

Figure 17:
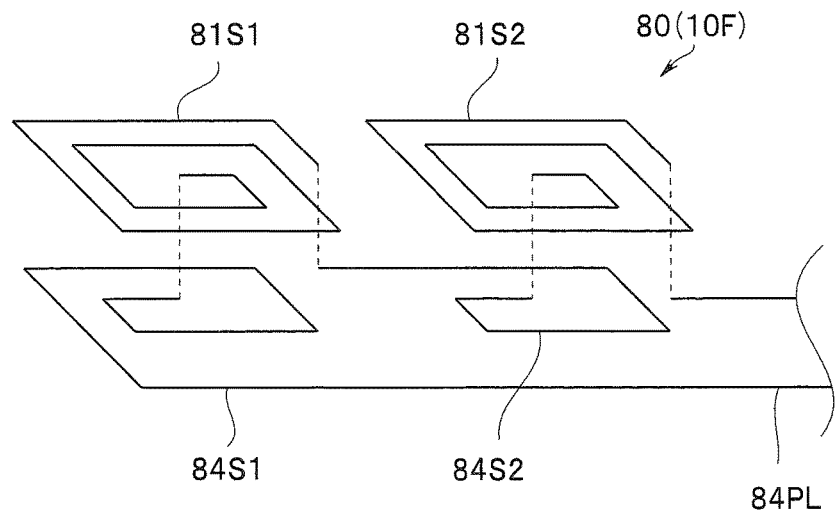
FIG. 17 is a connection diagram of four planar coils of the optical fiber scanning apparatus in the modification 3 of the second embodiment.

FIG. 17 illustrates a connection example of the four planar coils 84S1, 84S2, 81S1 and 81S2 configuring two multilayer coils of the coil unit 80. In the example illustrated in FIG. 17, the two multilayer coils generate the magnetic fields in the same direction. However, the magnetic fields in the opposite directions are generated depending on a connection state as already described.

The optical fiber scanning apparatus 10E can scan the optical fiber 28 with further lower power than the optical fiber scanning apparatus 10C.

Note that, similarly to the optical fiber scanning apparatus 10D, it is needless to say that the optical fiber scanning apparatus in which a coil chip with two planar coils disposed to one base body is flip-chip-mounted on the wiring board 64 has the same effects as the optical fiber scanning apparatuses 10D and 10F.

Third Embodiment

Figure 18:
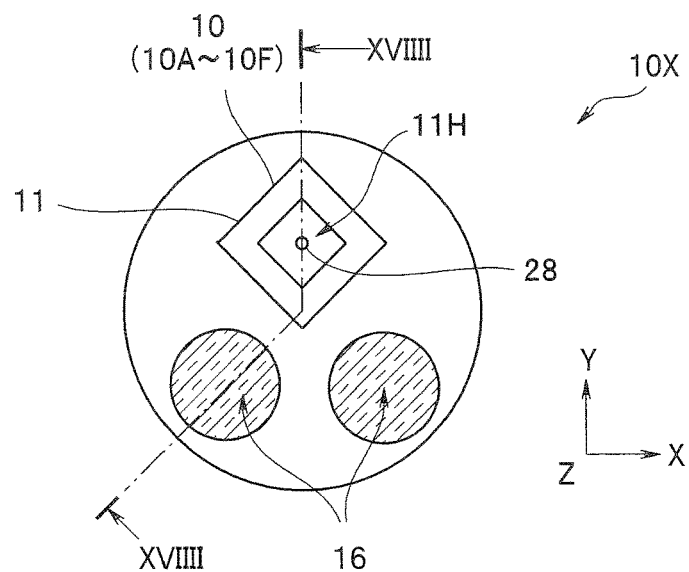
FIG. 18 is a sectional view in a long axis orthogonal direction of the optical fiber scanning apparatus in a third embodiment.
Figure 19:
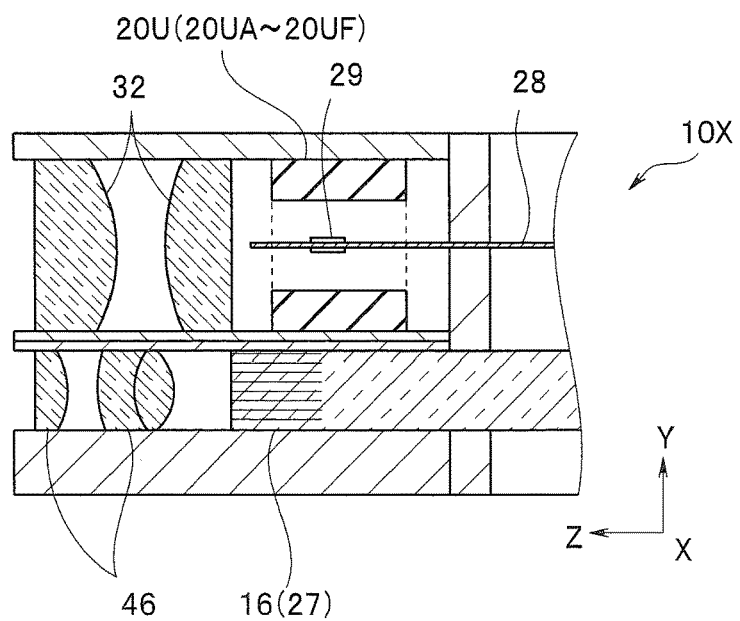
FIG. 19 is a sectional view along a XVIIII-XVIIII line in FIG. 18 of the optical fiber scanning apparatus in the third embodiment.

As illustrated in FIG. 18 and FIG. 19, while an optical fiber scanning apparatus 10X in the third embodiment is similar to the already described optical fiber scanning apparatuses 10 and 10A to 10F, two incidence portions 16 of a detection unit 176 (see FIG. 21) which detects reflected light of light with which an object is irradiated from the optical fiber 28 are arranged in the frame body 11.

Note that FIG. 18 is a sectional view in a long axis orthogonal direction of the optical fiber scanning apparatus 10X, and FIG. 19 is a sectional view along a XVIIII-XVIIII line in FIG. 18.

As illustrated in FIG. 18, the incidence portion 16 is a distal end portion of an optical fiber (also referred to as "detection fiber", hereinafter) 27 which guides the reflected light. The reflected light made incident from the distal end portion of the optical fiber 27 through a detection optical system 46 formed of a plurality of lenses is guided to a main body device 3 (see FIG. 20 and FIG. 21). Note that it is preferable that the optical fiber 27 is a fiber bundle formed of a plurality of optical fibers. In addition, there may be one incidence portion 16 or three or more incidence portions 16.

Here, the optical fiber 27 is considered as a part of the detection unit 176. In addition, a photodiode (PD) element or the like which detects the reflected light may be directly arranged in the frame body 11 as the incidence portion 16.

For the optical fiber scanning apparatus 10X, since the incidence portions 16 of the detection unit 176 are arranged in the frame body 11, a structure is simple as a whole and the diameter is small compared to the optical fiber scanning apparatus in which the incidence portion 16 is disposed to a different member.

Fourth Embodiment

Figure 20:
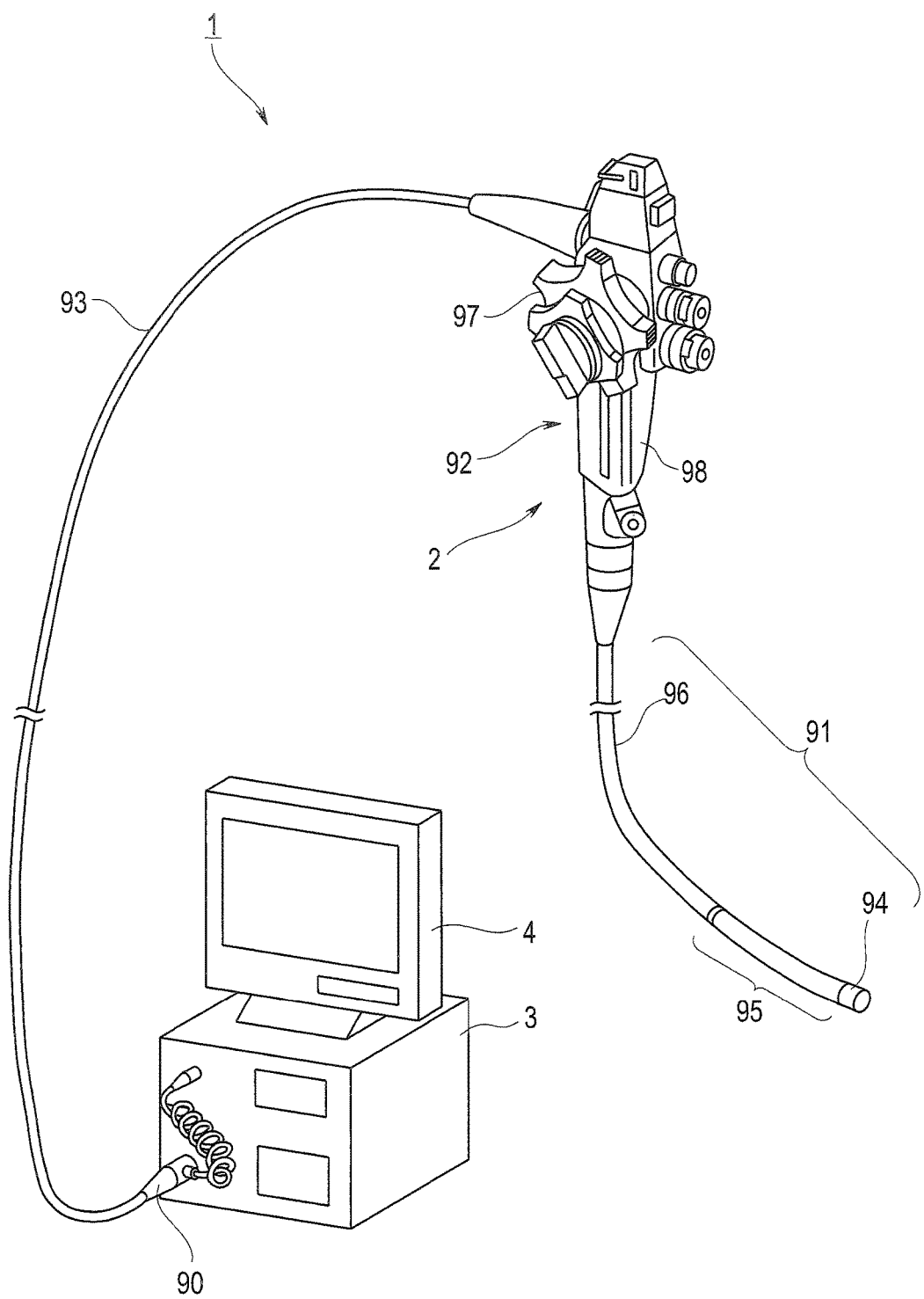
FIG. 20 is a perspective view of an endoscope system including an endoscope in a fourth embodiment.

An optical scanning type endoscope (referred to as "endoscope" hereinafter) 2 in the fourth embodiment illustrated in FIG. 20 has one of the already-described optical fiber scanning apparatuses 10 and 10A to 10X at a distal end portion 94 of an insertion portion 91. Hereinafter, the description will be given with the endoscope 2 including the optical fiber scanning apparatus 10 as an example.

An optical scanning type endoscope system (referred to as "endoscope system" hereinafter) 1 including the endoscope 2 is provided with the endoscope 2, the main body device 3 having functions of a light source device and a video processor, and a monitor 4. The endoscope 2 irradiates a subject with the illumination light while performing two-dimensional scanning by the optical fiber scanning apparatus 10, detects the reflected light (return light) from the subject, performs data processing in the main body device 3, and displays a generated subject image on the monitor 4.

The endoscope 2 is provided with an elongated insertion portion 91 to be inserted into a living body, an operation portion 92, and a universal cable 93 to which an electric cable or the like is inserted. The insertion portion 91 of the endoscope 2 includes the distal end portion 94, a bending portion 95, and a flexible tube portion 96. Note that, while the endoscope 2 of the embodiment is a so-called flexible endoscope, even a so-called rigid endoscope in which the insertion portion 91 is rigid has the effects described later.

To the operation portion 92, a bending operation knob 97 for performing a bending operation of the bending portion 95 is freely turnably disposed. A connection portion of the insertion portion 91 and the operation portion 92 is a grasping portion 98 to be grasped by a user.

The universal cable 93 extended from the operation portion 92 is connected with the main body device 3 through a connector 90. The main body device 3 is connected with the monitor 4 which displays an endoscope image.

Figure 21:
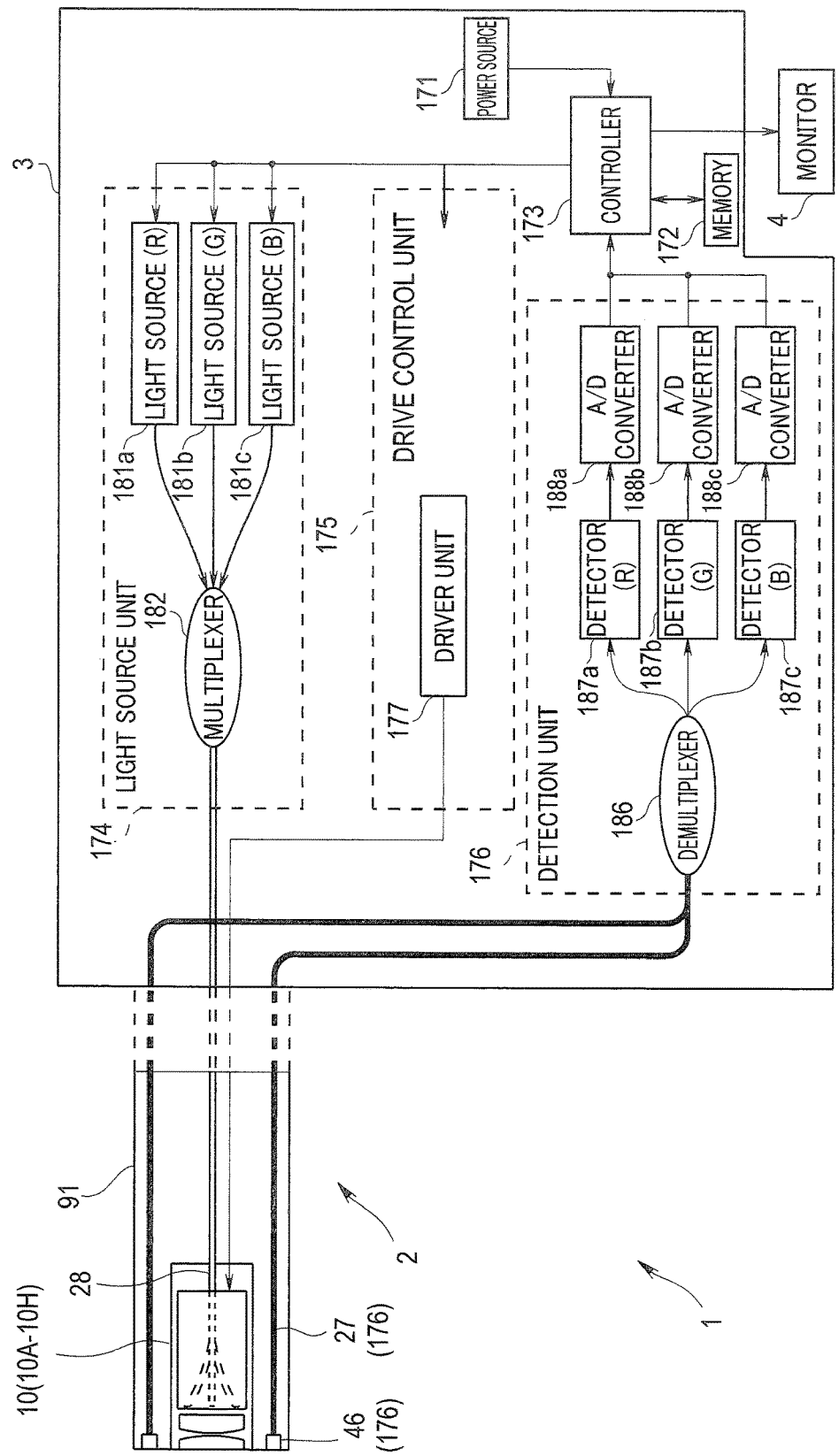
FIG. 21 is a block diagram of the endoscope system including the endoscope in the fourth embodiment.

Next, the configuration of the endoscope system 1 is illustrated in FIG. 21.

In the inside of the insertion portion 91 of the endoscope 2, the detection fiber 27 which is inserted from a proximal end side to the distal end side along an inner periphery of the insertion portion 91 and guides the reflected light from the subject is provided. To the incidence portion 16 which is a distal end of the detection fiber 27, the detection optical system 46 is disposed. When the connector 90 of the endoscope 2 is connected to the main body device 3, the detection fiber 27 is connected to a demultiplexer 186.

The main body device 3 is provided with a power source 171, a memory 172, a controller 173, a light source unit 174, the drive control unit 175, and the detection unit 176. The light source unit 174 is provided with three light sources 181a, 181b and 181c, and a multiplexer 182.

The drive control unit 175 is provided with a driver unit 177, and the optical fiber scanning apparatus 10 or the like is driven by the driver unit 177.

The power source 171 supplies power to the controller 173 or the like. In the memory 172, a control program for controlling the entire main body device 3 or the like is stored.

The controller 173 reads the control program from the memory 172, and controls the light source unit 174 and the drive control unit 175. In addition, the controller 173 performs control of performing data processing to light intensity signals of the reflected light from the object detected by the detection unit 176 and displaying the image on the monitor 4.

The light sources 181a, 181b and 181c of the light source unit 174 emit the light of respectively different wavelength bands, the light of the wavelength bands of R (red), G (green) and B (blue) for example, to the multiplexer 182, based on the control of the controller 173. The multiplexer 182 multiplexes the light of the wavelength bands of R, G and B, and emits it to the optical fiber 28.

The driver unit 177 of the drive control unit 175 outputs drive signals for causing the distal end of the optical fiber 28 of the optical fiber scanning apparatus 10 to perform scanning by a desired scanning method to the magnetic field generation unit 20U, based on the control of the controller 173. That is, the driver unit 177 outputs predetermined drive signals to the optical fiber scanning apparatus 10 so as to drive the distal end of the optical fiber 28 in a horizontal direction (X axis direction) and a vertical direction (Y axis direction) regarding an insertion axis (Z axis) of the insertion portion 91.

The detection fiber 27 receives the reflected light reflected on a surface of the subject, and guides the received reflected light to the demultiplexer 186. The demultiplexer 186 is a dichroic mirror or the like for example, and demultiplexes the reflected light by each predetermined wavelength band. Specifically, the demultiplexer 186 demultiplexes the reflected light guided by the detection fiber 27 into the reflected light of the wavelength bands of R, G and B, and outputs the respective reflected light to detectors 187a, 187b and 187c.

The detectors 187a, 187b and 187c are PD elements which detect light intensity of the reflected light of the wavelength bands of R, G and B respectively or the like. Signals of the light intensity detected in the detectors 187a, 187b and 187c are respectively outputted to A/D converters 188a, 188b and 188c. The A/D converters 188a to 188c respectively convert the signals of the light intensity outputted from the detectors 187a to 187c from analog signals to digital signals, and output the digital signals to the controller 173.

The controller 173 generates the object image by executing predetermined image processing to the digital signals from the A/D converters 188a to 188c, and displays the object image on the monitor 4.

Note that monochromatic light may be used or a laser beam may be used as the illumination light.

Since the optical scanning type endoscope 2 has one of the optical fiber scanning apparatuses 10 and 10A to 10F at the distal end portion 94 of the insertion portion 91, the distal end portion is small in the diameter and is lowly invasive. In addition, since the optical fiber scanning apparatuses 10 and 10A to 10F perform highly accurate scan irradiation, the optical scanning type endoscope 2 can obtain excellent images. In addition, since the optical scanning type endoscope 2 can efficiently drive the magnetic field generation unit, the power consumption is low.

The present invention is not limited to the individual embodiments described above, and various modifications, combinations and applications are of course possible without deviating from the scope of the invention.

What is claimed is:

1. An optical fiber scanning apparatus comprising:
   a frame body defining a cavity, a cross section of the cavity in a long axis direction is square, the cavity having an opening at a distal end;
   an optical fiber configured to emit illumination light from a distal end of the optical fiber, the distal end of the optical fiber being disposed in the cavity;
   a magnetic field generator disposed in the cavity of the frame body, the magnetic field generator comprising four coil units each including a separate flexible substrate, each separate flexible substrate having at least one planar coil, lead-out wiring layers of the at least one planar coil with an insulating layer, coil connection electrode pads and external connection electrode pads extended from a rear end of the lead-out wiring layers; and
   a permanent magnet disposed on a portion of the optical fiber arranged in the cavity, the permanent magnet being arranged in the cavity.

2. The optical fiber scanning apparatus according to claim 1, wherein each of the coil units comprise:
   a coil chip having a base body formed of silicon and the at least one planar coil disposed on the base body, the coil chip having a flip-chip mounting configuration for connection to the flexible substrate.

3. The optical fiber scanning apparatus according to claim 1, wherein each coil unit is a wiring board for which the planar coil, the lead-out wiring layer and the external connection electrode pad are disposed to the flexible substrate as an integrated conductor layer.

4. The optical fiber scanning apparatus according to claim 3, wherein a coil chip provided with a base body and a second planar coil disposed to the base body is flip-chip-mounted right above the at least one planar coil of the wiring board, and the at least one planar coil and the second planar coil are connected and configure a multilayer coil.

5. The optical fiber scanning apparatus according to claim 1, wherein the at least one planar coil comprises two planar coils lined in the long axis direction.

6. The optical fiber scanning apparatus according to claim 5, wherein, for each of the coil units, two coil chips are provided with a base body and each of the two coil chips include one of the two planar coils disposed to the base body the two coil chips being flip-chip-mounted on a wiring board for which the lead-out wiring layer and the external connection electrode pad are disposed to the flexible substrate as an integrated conductor layer.

7. The optical fiber scanning apparatus according to claim 5, wherein, for each of the coil units, a coil chip is provided with a base body and the two planar coils lined on the base body in the long axis direction the coil chip being flip-chip-mounted on a wiring board for which the lead-out wiring layer and the external connection electrode pad are disposed to the flexible substrate as an integrated conductor layer.

8. The optical fiber scanning apparatus according to claim 5, wherein each of the coil units is a wiring board for which the two planar coils are lined up in the long axis direction, and the lead-out wiring layer and the external connection electrode pad are disposed to the flexible substrate as an integrated conductor layer.

9. The optical fiber scanning apparatus according to claim 8, wherein each coil unit comprises first and second chips, the first and second coil chips being provided with a base body and a respective third and fourth planar coil is disposed to each base body the first and second coil chips being flip-chip-mounted right above a respective one of the two planar coils of the wiring board, and each of the two planar coils and each of the third and fourth planar coils are connected and configure a multilayer coil.

10. The optical fiber scanning apparatus according to claim 5, wherein the two planar coils of each of the coil units generate magnetic fields in a same direction.

11. The optical fiber scanning apparatus according to claim 5, wherein the two planar coils of each of the coil units generate magnetic fields in opposite directions.

12. The optical fiber scanning apparatus according to claim 3, further comprising an incidence portion of a detection sensor arranged at a distal end portion of the frame body, the detection sensor being configured to detect reflected light of the emitted illumination light.

13. The optical fiber scanning apparatus according to claim 12, wherein the incidence portion is a distal end portion of an other optical fiber configured to guide the reflected light.

14. An optical scanning type endoscope comprising:
    an insertion portion having a distal end portion; and
    the optical fiber scanning apparatus according to claim 1 disposed at the distal end portion of the insertion portion.

15. The optical fiber scanning apparatus according to claim 1, wherein the frame body is formed of metal.

16. The optical fiber scanning apparatus according to claim 1, wherein the frame body is formed of one of a stainless steel alloy and an aluminum alloy.

17. The optical fiber scanning apparatus according to claim 1, wherein the frame body is formed of a soft magnetic material.

* * * * *

UNITED STATES PATENT AND TRADEMARK OFFICE
CERTIFICATE OF CORRECTION

PATENT NO. : 10,502,947 B2
APPLICATION NO. : 15/337023
DATED : December 10, 2019
INVENTOR(S) : Mamoru Hasegawa et al.

It is certified that error appears in the above-identified patent and that said Letters Patent is hereby corrected as shown below:

In the Claims

Column 13, Claim 6, Line 51 should read:
include one of the two planar coils disposed to the base body, Column 14, Claim 7, Line 6 should read:
body in the long axis direction, the coil chip being flip-chip- Column 14, Claim 9, Line 20 should read:
to each base body, the first and second coil chips being Column 14, Claim 12, Line 32 should read:
claim 1, further comprising an incidence portion of a detec- Signed and Sealed this
Third Day of March, 2020

Andrei Iancu
*Director of the United States Patent and Trademark Office*